United States Patent [19]

Green et al.

[11] 4,036,959

[45] * July 19, 1977

[54] MICROBIOCIDAL CAPPED POLYMERS

[75] Inventors: Harold A. Green, Havertown, Pa.;
John J. Merianos, Jersey City;
Alfonso N. Petrocci, Glen Rock, both
of N.J.

[73] Assignee: Millmaster Onyx Corporation, New York, N.Y.

[ * ] Notice: The portion of the term of this patent subsequent to Jan. 6, 1993, has been disclaimed.

[21] Appl. No.: 623,402

[22] Filed: Oct. 17, 1975

Related U.S. Application Data

[63] Continuation-in-part of Ser. No. 518,596, Oct. 29, 1974, Pat. No. 3,931,319.

[51] Int. Cl.$^2$ .................... A01N 9/22; C07D 211/06

[52] U.S. Cl. .................... 424/248.56; 424/258; 424/267; 424/274; 424/329; 260/240 R; 260/247.5 R; 260/288 R; 260/293.87; 260/326.8

[58] Field of Search .................... 260/240 R, 240 E; 424/78, 248, 258, 267, 274, 248.56

[56] References Cited

U.S. PATENT DOCUMENTS

| 2,263,749 | 11/1941 | White et al. | 260/240 E |
| 3,931,319 | 1/1976 | Green et al. | 424/267 |

Primary Examiner—V. D. Turner
Attorney, Agent, or Firm—Arthur A. Jacobs

[57] ABSTRACT

Microbiocidal quaternary ammonium polymers which are made by condensing a difunctional tertiary amine with an excess of 1,4-dihalo-2-butene, then after removing the unreacted 1,4-dihalo-2-butene, adding to the reaction product a calculated quantity of a heterocyclic monofunctional tertiary amine for the purpose of forming a linear polymer whose termini at both ends are quaternary ammonium moieties.

4 Claims, No Drawings

MICROBIOCIDAL CAPPED POLYMERS

This is a continuation-in-part of co-pending application Ser. No. 518,596, filed Oct. 29, 1974, now U.S. Pat. No. 3,931,319.

This invention relates to a new class of microbiocidal agents. More particularly, this invention relates to linear quaternary ammonium polymers in which the quaternary ammonium moieties are part of the linear polymeric chain rather than appendages to, or part of, branches on the linear chain. Even more particularly, this invention relates to such linear polymeric quaternary chains in which the chains terminate in quaternary ammonium moieties, thereby making further chain progagation impossible. Such polymers may, therefore, be called "capped" polymers.

The products of this invention can be made by a two step reaction. In the first step, a difunctional tertiary amine is condensed with slightly more than the molar equivalent of a 1,4-dihalo-2-butene, after which the unreacted dihalo compound is removed, and the reaction is completed in a second step by adding a calculated quantity of monofunctional tertiary amine. A slight excess of the dihalo compound is required in the first step.

If the difunctional amine is represented by N(R')(R'') ZN (R') (R'') and the 1,4-diahalo-2butene by X—CH$_2$—CH=CH—CH$_2$—X, where X is a halogen, then when the 1,4-dihalo-2-butene is not in excess, the first step of the reaction may be represented by the chemical equation:

$$n(R')(R'')N-Z-N(R')(R'') + nX-CH_2-CH=CHCH_2X$$

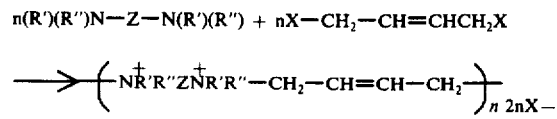

where X is a halogen such as chlorine or bromine, where n is an integer from about 2 to about 30; where R' and R'' may be either (1) a primary or secondary alkyl radical having from 1 to 20 carbon atoms, (2) hydroxy or dihydroxy derivatives of R' and R'', (3) benzyl, or (4) benzyl containing at least one alkyl group bonded to the benzene ring but where the sum of the carbon atoms on all such alkyl groups is less than 7; where Z consists of from one to three aliphatic divalent radicals, each of which has 2 to 10 carbon atoms, each aliphatic radical containing 0 to 2 double bonds and 0 to 2 hydroxy substituents; where the group (R') (R'') N, taken together, may be N-piperidino, N-pyrolidino, N-morpholino or N-homopiperidino; and where the group (R') (R'')-N-Z-N-(R') (R''), taken together, may be N,N'-di-lower alkyl piperazine or 1,4diazabicyclo (2.2.2) octane.

However, in the presence of a relatively small excess of 1,4-dihalo-2-butene, the terminal atoms of the linear polymeric product of the first step are halogen atoms, the product being:

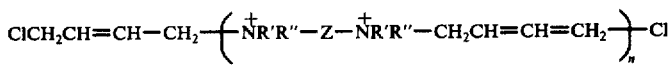

where the symbols have the same value or meaning as above.

Since these linear polymeric chains contain active halogen termini, the chains can be made to propogate if more difunctional tertiary amine is added to the reaction container already holding an excess of 1,4-dihalo-2-butene. However, if the unreacted dichloro compound is extracted and a monofunctional tertiary amine is added to the reaction container after the excess dichloro compound is removed, then it reacts with the two terminal halogen atoms of the linear chain to form two terminal quaternary moieties.

This latter reaction constitutes the second step of the process of the present invention, and may be represented as follows:

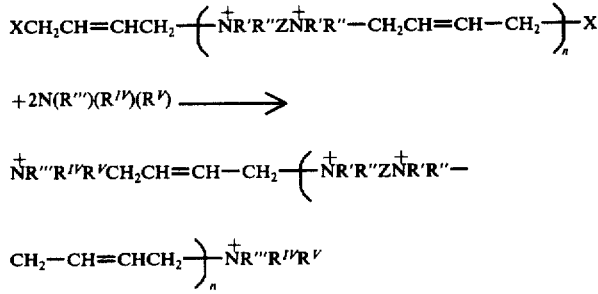

where R''', R$^{IV}$ and R$^V$ may be either (1) primary or secondary alkyl containing from 1 to 20 carbon atoms, or (2) hydroxyethyl, where the group (R''') (R$^{IV}$) (R$^V$) N, taken together may be either N-lower alkyl morpholino, quinolino, N-lower alkyl pyrrolidino, N-lower alkyl piperidino, N-lower alkyl homopiperidino, N-lower alkyl isoquinolino, and N,N-di-lower alkyl benzylamino; and where the other symbols have the same value or meaning as described previously.

The following examples are illustrative of the present invention:

EXAMPLE 1

To 42.6 grams of 1,4-bis-(dimethylamino)-2-butene (0.3 mole) dissolved in 100 ml. of water, there was added dropwise 50.0 grams of 1,4-dichloro-2-butene (0.4 mole) with constant stirring. The rate of addition was maintained at a rate to keep the exothermic reaction at a temperature of 60° to 70° C. When addition was complete, the reaction mixture was heated on a steam bath at about 90° C to 95° C for more than 2 hours. Then it was cooled to 20° C and extracted with three 100 ml. portions of ethyl ether to remove the unreacted 1,4-dichloro-2-butene, and the residue warmed in vacuo to remove ether from the layer containing the polyquaternary.

The polyquaternary aqueous layer was analyzed for total chlorine, and also for ionic chloride. The difference represented the quantity of terminal chlorine atoms on the polymeric chains.

The calculations showed that the equivalent of 0.03 moles of chlorine terminal atoms remained in the polyquaternary chains. Therefore, 4.75 grams of octyl dimethyl amine (0.03 mole) was added to the aqueous layer, and the mixture heated on a steam bath for 2 more hours at about 90° to 95° C. The reaction mixture was analyzed for total polymer quaternary content, and the concentration was adjusted to 50% active polyquaternary.

The experiment was repeated using petroleum ether instead of ethyl ether to extract the excess dichloro compound. The similar results indicated that any inactive organic solvent may be used to extract the unreacted 1,4-dichloro-2-butene.

EXAMPLE 2

In addition to the compound of Example 1, the following capped polymers were made by substituting other tertiary amines for octyl dimethyl amine, using the procedure of Example 1. They were as follows:

a. the polymeric quaternary formed by the reaction of 1,4-bis-(dimethylamino)-2-butene and 1,4-dichloro-2-butene, capped by decyl dimethyl amine.
b. the polymeric quaternary formed by the reaction of 1,4-bis-(dimethylamino)-2-butene and 1,4-dichloro-2-butene, capped by dodecyl dimethyl amine.
c. the polymeric product formed by the reaction of 1,4-bis-(dimethylamino)-2-butene and 1,4-dichloro-2-butene, capped by tetradecyl dimethyl amine.
d. the polymeric product formed by the reaction of 1,4-bis-(dimethylamino)-2-butene and 1,4-dichloro-2-butene, capped by hexadecyl dimethyl amine.

EXAMPLE 3

The following tertiary amines were also used to cap the polymeric quaternary of 1,4-bis-(dimethylamino)-2-butene and 1,4-dichloro-2-butene using the procedure shown in Example 1:

(a) propyl dimethyl amine, (b) butyl dimethyl amine, (c) pentyl dimethyl amine, (d) hexyl dimethyl amine, (e) dibutyl methyl amine, (f) didecyl methyl amine, and (g) di-octyl methyl amine.

Microbiocidal evaluations were made as follows:

EXAMPLE 4

Each potential microbiocidal capped quaternary ammonium polymer to be tested was dissolved in distilled water to the test concentration, and was added aseptically to previously sterilized cotton-stoppered 125 ml. Erlenmeyer flasks.

One set of flasks containing the potential microbiocide at concentrations of 25 ppm, 50 ppm, 75 ppm, 100 ppm, 150 ppm, 200 ppm, 250 ppm, and 300 ppm was inoculated by introducing into each flask 0.5 ml of a 1/10 nutrient broth dilution of a 24 hour nutrient broth culture of Aerobacter aerogenes. Another set of test flasks containing the potential microbiocide at similar concentrations was inoculated by introducing into each flask 0.5 ml. of a 1/10 nutrient broth culture of Pseudomonas aeruginosa.

At intervals of 30, 60 and 180 minutes following inoculation, a 1 ml. aliquot was withdrawn from each flask and added to 9 ml. of sterile azolectin/"Tween 80" neutralizer from which tenfold serial dilutions were prepared in the sterile neutralizer solution.

Agar plates were prepared from $1 \times 10^{-2}$ and $1 \times 10^{-3}$ dilutions.

Simultaneously with each set of test flasks, a control of sterile distilled water was similarly inoculated, and aliquots were taken at the same time intervals and plated at $1 \times 10^4$, $1 \times 10^5$, and $1 \times 10^6$ dilutions.

A comparison of the surviving organisms for various test concentrations of the test material at different time intervals was made and tabulated.

The results were as follows:

Table 1

Number of survivors of A. Aerogenes following exposure to various capped polyquaternaries at different concentrations for varying periods of time.

| Compound | Concentration in ppm | No. of Surviving Organisms/ml $\times$ 102 | | |
|---|---|---|---|---|
| | | after 30 Min. | 60 Min. | 180 Min. |
| Example 1 | 50 | 45 | 10 | 0 |
| | 75 | 24 | 4 | 0 |
| Example 2(a) | 50 | 72 | 9 | 0 |
| | 75 | 46 | 6 | 0 |
| Example 2(b) | 50 | 24 | 6 | 0 |
| | 75 | 12 | 5 | 0 |
| Example 2(c) | 50 | 37 | 14 | 0 |
| | 75 | 28 | 10 | 0 |
| Example 2(d) | 50 | 56 | 29 | 0 |
| | 75 | 24 | 13 | 0 |
| Untreated Control | | 45,000 | 55,000 | 111,000 |

Table 2

Number of survivors of P. aeruginosa following exposure to various capped polyquaternaries at different concentrations for varying periods of time.

| Compound | Concentration in ppm | No. of Surviving Organisms/ml $\times$ 102 | | |
|---|---|---|---|---|
| | | After 30 Min. | 60 Min. | 180 Min. |
| Example 1 | 50 | 940 | 466 | 0 |
| | 75 | 480 | 275 | 0 |
| | 100 | 84 | 26 | 0 |
| Example 2(a) | 50 | 750 | 205 | 0 |
| | 75 | 230 | 140 | 0 |
| | 100 | 105 | 44 | 0 |
| Example 2(b) | 50 | 695 | 137 | 0 |
| | 75 | 192 | 59 | 0 |
| | 100 | 82 | 30 | 0 |
| Example 2(c) | 50 | 746 | 150 | 0 |
| | 75 | 412 | 81 | 0 |
| | 100 | 65 | 17 | 0 |
| Example 2(d) | 50 | 746 | 176 | 0 |
| | 75 | 390 | 89 | 0 |
| | 100 | 74 | 26 | 0 |
| Untreated Control | | 40,000 | 65,000 | 90,000 |

EXAMPLE 5

The following tertiary amines were also used to cap the polymeric quaternary made from 1,4-bis-(dimethylamino)-2-butene and 1,4-dichloro-2-butene, using the procedure described in Example 1: (a) N-methyl morpholine; (b) quinoline; (c) N-methyl homopiperidine; (d) N,N-dimethyl benzylamine; (e) N-methyl pyrrolidine; (f) N-methyl piperidine; and (g) isoquinoline.

EXAMPLE 6

Illustrative of all the heterocyclic compounds described above, compounds (a) and (b) of Example 5 were assayed bacteriologically by the Standard Broth Dilution Method in order to ascertain the Minimum Inhibitory Level, that is, the lowest concentration of test material which prevents macroscopic growth.

Aliquots of a solution of each compound were added to appropriate broth culture media contained in test tubes, so that a range of concentrations of each compound was obtained.

The tubes so prepared were inoculated with either 24 hour broth cultures of test bacteria, or 14 day aqueous spore suspensions of test fungi.

The tubes were incubated as follows:
Bacteria: 72 hours at 37° C.
Fungi: 14 days at 28° C.

Following incubation, the tubes were examined for the presence or absence of macroscopic growth.

The test organisms employed were:
Bacteria:
*Escherichia coli* (E.c.)
*Pseudomonas aeruginosa* (Ps.a.)
*Staphylococcus aureus* (S.a.)
*Streptococcus faecalis* (S.f.)
Fungi:
*Aspergillus niger* (A.n.)
*Penicilium expansum* (P.e.)

Following are the Minimum Inhibitory Concentrations of the compounds that were tested in parts per million:

Table 3

| Compound | Bacteria Gram Neg. | | Gram Pos. | | Fungi | |
|---|---|---|---|---|---|---|
|  | E.c. | Ps.a. | S.a. | S.f. | A.n. | P.e. |
| Example 5(a) | 50 | 50 | 50 | 100 | 1000 | 1000 |
| Example 5(b) | 50 | 50 | 50 | 500 | 1000 | 1000 |

The results of these tests show that the capped polyquaternary ammonium products are very effective microbiocides in concentrations at least as low as 50 ppm.

The invention claimed is:

1. The compound

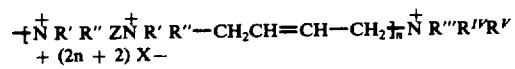

wherein R' and R" are selected from the group consisting of (a) primary or secondary alkyls having 1 to 20 carbon atoms, (b) hydroxy or dihydroxy derivatives of R' and R", (c) benzyl, and (d) benzyl having at least one alkyl group bonded to the benzene ring, with the total sum of alkyl carbon atoms attached to the benzene ring being less than 7; wherein (R'''), (R$^{IV}$) and (R$^V$), taken together with N, form a heterocyclic amino radical selected from the group consisting of N-lower alkyl morpholino, quinolino, N-lower alkyl pyrrolidino, N-lower alkyl piperidino, N-lower alkyl homopiperidino, N-lower alkyl isoquinolino, and N,N-di-lower alkyl benzylamino; wherein Z consists of 1 to 3 aliphatic divalent radicals, each of which has 2 to 10 carbon atoms with each aliphatic radical containing 0 to 2 double bonds and 0 to 2 hydroxy substituents; wherein X is selected from the group consisting of chlorine and bromine; and wherein $n$ is an integer of about 2 to about 30.

2. The compound of claim 1 wherein each N-lower alkyl is methyl.

3. A method of inhibiting the growth of microorganisms selected from the group consisting of bacteria and fungi which comprises applying to said microorgansims an effective amount for inhibiting said microorganisms of the compound of claim 1.

4. A method of inhibiting the growth of microorganisms selected from the group consisting of bacteria and fungi which comprises applying to said microorganisms an effective amount for inhibiting said microorganisms of the compound of claim 2.

* * * * *